(12) United States Patent
Lee et al.

(10) Patent No.: US 12,045,977 B2
(45) Date of Patent: Jul. 23, 2024

(54) DISEASE DIAGNOSIS SYSTEM AND METHOD USING MULTIPLE COLOR MODELS AND NEURAL NETWORK

(71) Applicant: DEEP BIO INC., Seoul (KR)

(72) Inventors: Sang Hun Lee, Seoul (KR); Sun Woo Kim, Seongnam-si (KR)

(73) Assignee: DEEP BIO INC., Seoul (KR)

( * ) Notice: Subject to any disclaimer, the term of this patent is extended or adjusted under 35 U.S.C. 154(b) by 442 days.

(21) Appl. No.: 17/266,103

(22) PCT Filed: Aug. 7, 2019

(86) PCT No.: PCT/KR2019/009846
§ 371 (c)(1),
(2) Date: Feb. 4, 2021

(87) PCT Pub. No.: WO2020/032561
PCT Pub. Date: Feb. 13, 2020

(65) Prior Publication Data
US 2021/0295509 A1 Sep. 23, 2021

(30) Foreign Application Priority Data
Aug. 7, 2018 (KR) .................. 10-2018-0092033

(51) Int. Cl.
*G06T 7/90* (2017.01)
*G06N 3/10* (2006.01)
(Continued)

(52) U.S. Cl.
CPC ............. *G06T 7/0012* (2013.01); *G06N 3/10* (2013.01); *G06T 7/90* (2017.01); *G16H 30/20* (2018.01);
(Continued)

(58) Field of Classification Search
CPC .................. G06T 7/0012; G06T 7/90; G06T 2207/10024; G06T 2207/20021;
(Continued)

(56) References Cited

U.S. PATENT DOCUMENTS

| | | | |
|---|---|---|---|
| 9,282,929 B2 | 3/2016 | Choi et al. | |
| 2005/0165290 A1 | 7/2005 | Kotsianti et al. | |

(Continued)

FOREIGN PATENT DOCUMENTS

| | | |
|---|---|---|
| CN | 106373137 | 2/2017 |
| JP | 2013238459 | 11/2013 |

(Continued)

OTHER PUBLICATIONS

International Search Report dated Jan. 28, 2020, issued in International Application No. PCT/KR2019/009846 (with English Translation).

(Continued)

*Primary Examiner* — Charlotte M Baker
(74) *Attorney, Agent, or Firm* — PnK IP LLC

(57) ABSTRACT

A disease diagnosis system implemented in a system including a processor and which uses the neural network and a slide on which biological tissue is provided and from which a biological image is obtained, the system including: a pre-processing module for generating first to Kth image information corresponding to each of a plurality of patches obtained by dividing the slide into a predetermined size, wherein ith image information, $1<=i<=K$, includes at least one channel value corresponding to an ith color model, and a first color model to a Kth color model are different from each other; and a patch neural network which receives the first image information to the Kth image information cor- (Continued)

responding to each of the plurality of patches, so as to output a patch-level diagnosis result indicating whether a disease exists in each patch.

15 Claims, 7 Drawing Sheets

(51) Int. Cl.
 *G06T 7/00* (2017.01)
 *G16H 30/20* (2018.01)
 *G16H 30/40* (2018.01)
 *G16H 50/20* (2018.01)
 *G16H 50/70* (2018.01)
(52) U.S. Cl.
 CPC ............ *G16H 30/40* (2018.01); *G16H 50/20* (2018.01); *G16H 50/70* (2018.01); *G06T 2207/10024* (2013.01); *G06T 2207/20021* (2013.01); *G06T 2207/20081* (2013.01); *G06T 2207/20084* (2013.01); *G06T 2207/30024* (2013.01)
(58) Field of Classification Search
 CPC . G06T 2207/20081; G06T 2207/20084; G06T 2207/30024; G06N 3/10; G16H 30/20; G16H 30/40; G16H 50/20; G16H 50/70; G16H 50/30

USPC ........................................................ 382/128
 See application file for complete search history.

(56) References Cited

U.S. PATENT DOCUMENTS

2014/0233826 A1 8/2014 Agaian et al.
2018/0114317 A1 4/2018 Song et al.

FOREIGN PATENT DOCUMENTS

| KR | 10-2014-0093376 | 7/2014 |
| KR | 10-2016-0034814 | 3/2016 |
| KR | 10-2016-0168176 | 6/2018 |
| KR | 10-2018-0066983 | 6/2018 |
| WO | 2013049153 | 4/2013 |
| WO | 2018076023 | 4/2018 |

OTHER PUBLICATIONS

Liu, Yun & Gadepalli, Krishna & Norouzi, Mohammad & Dahl, George & Kohlberger, Timo & Boyko, Aleksey & Venugopalan, Subhashini & Timofeev, Aleksei & Nelson, Philip & Corrado, G.s & Hipp, Jason & Peng, Lily & Stumpe, Martin. (2017). Detecting Cancer Metastases on Gigapixel Pathology Images.

Jimenez et al., "Convolutional neural networks for an automatic classification of prostate tissue slides with high-grade Gleason score," Proc. of SPIE, vol. 10140, pp. 1-9.

|  | accuracy | precision= PPV | sensitiviey= recall | specificity |
|---|---|---|---|---|
| train (62358:108300) | 0.9913 | 0.9957 | 0.9805 | 0.9975 |
| val (8963:15499) | 0.9825 | 0.9965 | 0.9556 | 0.9981 |
| test (14898:19089) | 0.9770 | 0.9891 | 0.9582 | 0.9917 |

|  | accuracy | precision= PPV | sensitiviey= recall | specificity |
|---|---|---|---|---|
| train (478:218) | 0.9296 | 0.9447 | 0.9545 | 0.8732 |
| val (117:57) | 0.9368 | 0.9550 | 0.9464 | 0.9194 |
| test (1302:1658) | 0.9213 | 0.9199 | 0.8994 | 0.9385 |

DISEASE DIAGNOSIS SYSTEM AND METHOD USING MULTIPLE COLOR MODELS AND NEURAL NETWORK

CROSS REFERENCE TO RELATED APPLICATION

This application is a National Stage Entry of International Application No. PCT/KR2019/009846, filed on Aug. 7, 2019, and claims priority from and the benefit of Korean Patent Application No. 10-2018-0092033, filed on Aug. 7, 2018, each of which is hereby incorporated by reference for all purposes as if fully set forth herein

TECHNICAL FIELD

The present invention relates to a disease diagnosis system using multiple color models and a neural network and a method thereof. More specifically, the present invention relates to a system and method, which can diagnose a predetermined disease (e.g., prostate cancer) by performing learning through a neural network and inputting an image of a biological tissue using the learned neural network in the form of various different color models.

DISCUSSION OF THE BACKGROUND

One of major tasks performed by pathology or a pathology department is to read a patient's biometric image and perform diagnosis for determining a state or symptom of a specific disease. Performing such a diagnosis like this requires a method that depends on the experience and knowledge of medical personnel skilled for an extended period of time.

Recently, attempts of automating the tasks such as recognizing or classifying images using a computer system have been made actively owing to advancement in machine learning. Particularly, attempts have been made to automate diagnosis performed by skilled medical personnel using a neural network (e.g., a deep learning method using a convolution neural network (CNN)), which is a kind of machine learning.

Particularly, diagnosis through deep learning using a neural network (e.g., CNN) sometimes finds out characteristics of disease factors unknown to experienced medical personnel from an image in that it does not simply automate the experience and knowledge of the experienced medical personnel, but finds out characteristic factors through self-learning and derives a desired answer.

Generally, diagnosis of a disease through a neural network using a biometric image uses a piece of biometric image, i.e., a patch (or also referred to as a tile) obtained from biological tissue provided on a slide. That is, a skilled medical practitioner annotates the state of a specific disease (e.g., whether cancer is expressed) with regard to a corresponding tile, and trains the neural network using a plurality of annotated tiles as training data. In this case, a convolution neural network may be used as the neural network.

However, in this method, the trained neural network determines the state of a disease of a corresponding tile on the basis of image features of the tile. In practice, when the state of a specific biological tissue is determined for a specific disease, there are cases in which even the current state of the tissues around a specific biological tissue (e.g., the shape, whether a specific pattern exists, etc.) should be considered, in addition to the specific biological tissue itself. However, there is a problem in that the conventional method is not suitable in this case.

Meanwhile, in the conventional learning method, the color itself of a biometric image or a patch is input as an input data. For example, when the biometric image or patch is in Red, Green and Blue (RGB) format, an input data defined by three channel values of RGB is used as it is. However, in this case, the color of a tissue being dyed may be different according to the characteristics of a dyeing reagent used for dyeing a biological tissue corresponding to the biometric image, and this may directly affect a trained neural network.

Accordingly, a neural network needs to be trained in a manner more robust to nonfundamental color features according to dyeing or the like, which are not the fundamental image features of a tissue.

It is to be understood that both the foregoing general description and the following detailed description are exemplary and explanatory and are intended to provide further explanation of the invention as claimed.

SUMMARY

Therefore, the present invention has been made in view of the above problems, and an aspect of the invention provides a diagnosis system using a neural network and a method thereof, which may have a characteristic robust to color, not the image features fundamental to diagnosing whether or not a disease is expressed, by using multiple color models.

Another aspect of the invention provides a diagnosis system using a neural network and a method thereof, which can further increase accuracy by using even surrounding tiles, as well as a specific tile, for learning in order to determine a state of disease of the specific tile (e.g., whether or not a disease is expressed, or an index indicating the state of a disease).

Another aspect of the invention provides a diagnosis system and a method thereof, which can effectively and accurately diagnose whether a disease is expressed in a wide range of biological tissues including a corresponding patch using a diagnosis result of each patch, not the diagnosis result itself of each patch.

To accomplish the above aspects, according to one embodiment of the invention, there is provided a disease diagnosis system implemented in a system including a processor and a storage device storing a neural network, and using a slide of which a biometric image is obtained therefrom, and the neural network, the system including: a preprocessing module for generating, for each of a plurality patches generated by dividing the biometric image obtained from the slide in a predetermined size, first image information to K-th image information (here, K is an integer equal to or greater than 2) corresponding to the patch, wherein i-th image information (i is an arbitrary integer of $1<=i<=K$), and that is configured of at least one channel value corresponding to an i-th color model, and in which all of a first color model to a K-th color model are different color models; and a patch neural network for receiving, for each of the plurality of patches, the first image information to the K-th image information corresponding to the patch for an input layer, and outputting a patch-level diagnosis result indicating whether a disease exists in the corresponding patch.

In an embodiment, each of the first color model to the K-th color model may be any one among an RGB model, an HSV model, a CMYK model, a YCbCr model, and a Gray model.

In an embodiment, the disease diagnosis system may further comprise a slide diagnosis engine for marking a patch determined as cancer as a result of patch-level diagnosis on each of the plurality of patches included in the slide, and outputting a slide-level diagnosis result indicating whether a disease exists in the slide on the basis of the marked result.

In an embodiment, the slide diagnosis engine may form a plurality of clusters by clustering the patches determined as cancer in a predetermined manner, receive a plurality of cluster features as input values for each of the formed clusters, and output the slide-level diagnosis result of the slide including the clusters.

In an embodiment, the disease may be prostate cancer.

According to another aspect of the invention, there is provided a disease diagnosis system implemented in a system including a processor and a storage device storing a neural network, and using a slide of which biological tissue is disposed thereon and of which a biometric image is obtained therefrom, and the neural network, the system including: a patch neural network for receiving, for each of a plurality of patches generated by dividing the slide in a predetermined size, first image information to K-th image information corresponding to the patch for an input layer, and outputting a patch-level diagnosis result indicating whether a disease exists in the corresponding patch; and a slide diagnosis engine for marking a patch determined as cancer as a result of patch-level diagnosis on each of the plurality of patches included in the slide, and outputting a slide-level diagnosis result indicating whether a disease exists in the slide on the basis of the marked result, wherein i-th image information (i is an arbitrary integer of $1 \leq i \leq K$) is configured of at least one channel value corresponding to an i-th color model, and all of a first color model to a K-th color model are different color models.

According to another aspect of the invention, there is provided a disease diagnosis method implemented in a system including a processor and a storage device storing a neural network, and using a slide of which biological tissue is disposed thereon and of which a biometric image is obtained therefrom, and the neural network, the method comprising the steps of: generating, for each of a plurality of patches generated by dividing the slide in a predetermined size, first image information to K-th image information (here, K is an integer equal to or greater than) corresponding to the patch, wherein i-th image information (i is an arbitrary integer of $1 \leq i \leq K$) is configured of at least one channel value corresponding to an i-th color model, and all of a first color model to a K-th color model are different color models; and receiving, for each of the plurality of patches, the first image information to the K-th image information corresponding to the patch for an input layer, and outputting, by the system, a patch-level diagnosis result indicating whether a disease exists in the patch.

In an embodiment, each of the first color model to the K-th color model may be any one among an RGB model, an HSV model, a CMYK model, a YCbCr model, and a Gray model.

In an embodiment, the disease diagnosis method may further comprise the step of marking a patch determined as cancer as a result of patch-level diagnosis on each of the plurality of patches included in the slide, and outputting, by the system, a slide-level diagnosis result indicating whether a disease exists in the slide on the basis of the marked result.

In an embodiment, the step of outputting a slide-level diagnosis result may include the steps of: forming a plurality of clusters by clustering the patches determined as cancer in a predetermined manner; and receiving a plurality of cluster features as input values for each of the formed clusters, and outputting the slide-level diagnosis result of the slide including the clusters.

According to another aspect of the invention, there is provided a disease diagnosis method implemented in a system including a processor and a storage device storing a neural network, and using a slide of which biological tissue is disposed thereon and of which a biometric image is obtained therefrom, and the neural network, the method including the steps of: receiving, for each of a plurality of patches generated by dividing the slide in a predetermined size, first image information to K-th image information corresponding to the patch for an input layer, and outputting a patch-level diagnosis result indicating whether a disease exists in the patch; and marking a patch determined as cancer as a result of patch-level diagnosis on each of the plurality of patches included in the slide, and outputting, by the system, a slide-level diagnosis result indicating whether a disease exists in the slide on the basis of the marked result, wherein i-th image information (i is an arbitrary integer in the range of $1 \leq i \leq K$) is configured of at least one channel value corresponding to an i-th color model, and all of a first color model to a K-th color model are different color models.

According to another aspect of the invention, there is provided a computer program installed in a data processing device and recorded in a medium for performing the method described above.

According to one or more embodiments of the invention, as a channel value corresponding to another color model (e.g., an HSV 3 channel value, a gray channel value, etc.), as well as an input data, i.e., a color value corresponding to an original color model of a patch (e.g., RGB 3 channel values), is additionally used as an input data, there is an effect of having a characteristic robust to variations according to various factors of color, not the image features fundamental to diagnosing whether a disease is expressed, while reflecting well image features related to a disease expressed by a color difference.

In addition, according to embodiments of the invention, since there is provided a neural network which can determine a disease state of a specific patch considering a macro patch including the specific patch and further including surrounding patches while performing diagnosis on the specific patch, there is an effect of providing a higher diagnosis accuracy.

In addition, according to embodiments of the invention, as whether a disease is expressed on a slide including a corresponding patch is determined again using a cluster and features of the cluster to solve a problem that occurs when it is determined that the disease is expressed in the slide including the patch only on the basis of a diagnosis result of each patch, there is an effect of performing diagnosis effectively and accurately.

BRIEF DESCRIPTION OF THE DRAWINGS

To more sufficiently understand the drawings cited in the detailed description of the present invention, a brief description of each drawing is provided.

DETAILED DESCRIPTION

Figure 1:
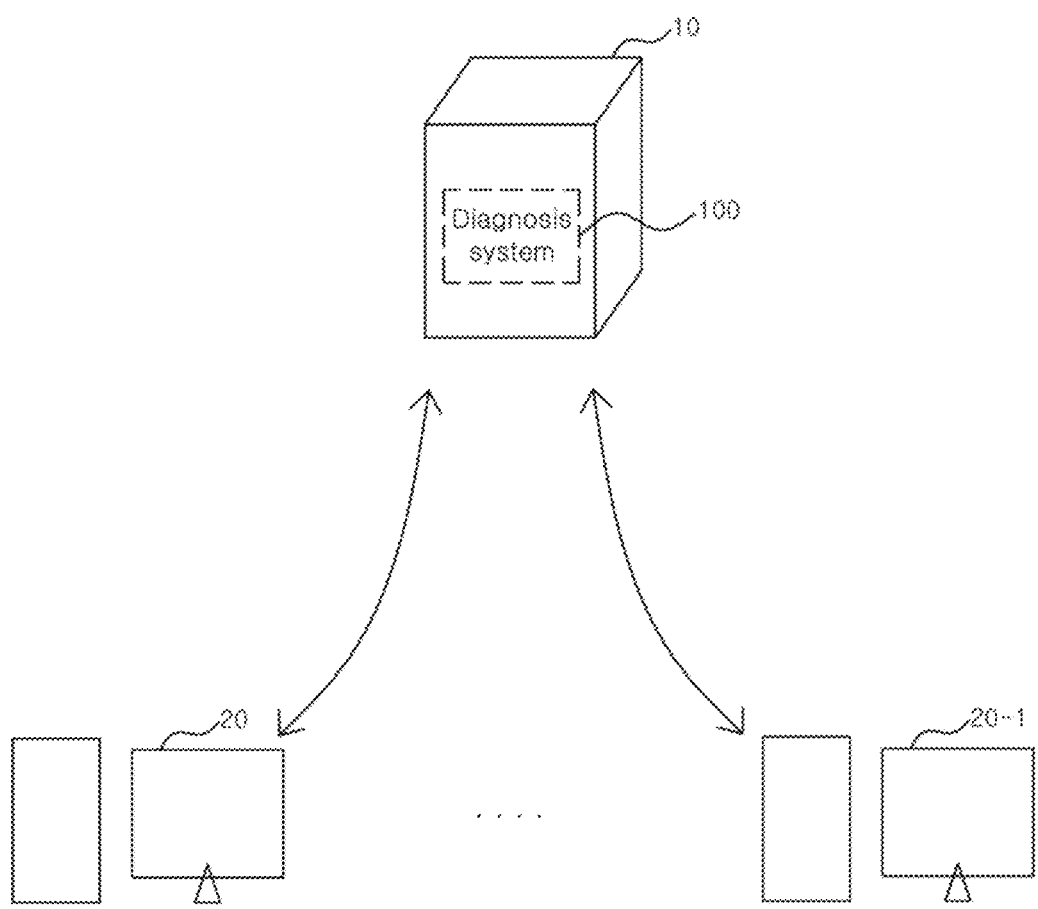
FIG. 1 is a view showing a schematic system configuration of a disease diagnosis system using multiple color models and a neural network constructed according to principles of the invention.

As the present invention may apply various modifications and have various embodiments, specific embodiments will be illustrated in the drawings and described in detail in the detailed description. However, this is not intended to limit the present invention to the specific embodiments, and it should be understood to include all modifications, equivalents, and substitutes included in the spirit and scope of the present invention. In describing the present invention, when it is determined that detailed description of a related known technology may obscure the subject matter of the present invention, the detailed description will be omitted.

Although the terms such as first, second and the like may be used to describe various components, the components should not be limited by the terms. These terms are only used for the purpose of distinguishing one component from the other components.

The terms used in the present application are only used to describe specific embodiments, and are not intended to limit the present invention. Singular expressions include plural expressions unless the context clearly indicates otherwise.

In this specification, the terms such as "comprise" or "have" are intended to designate the presence of features, numbers, steps, actions, components, parts, or combinations thereof described in the specification, and it should be understood that they do not preclude the possibility of the presence or addition of one or more other features or numbers, steps, actions, components, parts, or combinations thereof.

In addition, in this specification, when any one component 'transmits' data to another component, this means that the component may directly transmit the data to another component, or may transmit the data to another component through at least one other component. On the contrary, when one component 'directly transmits' data to another component, it means that the data is transmitted from the component to another component without passing through the other components.

Hereinafter, the present invention will be described in detail focusing on the embodiments of the present invention with reference to the accompanying drawings. The same reference numerals in each drawing indicate the same members.

FIG. 1 is a view showing a schematic system configuration of a disease diagnosis system using multiple color models and a neural network constructed according to principles of the invention.

Referring to FIG. 1, a disease diagnosis system 100 (hereinafter, a diagnosis system) using multiple color models and a neural network constructed according to principles of the invention may be installed in a predetermined server 10 to implement one or more embodiments of the invention. The server 10 corresponds to a data processing device having a computing ability for implementing one or more embodiments of the invention, and those skilled in the art may easily infer that any device capable of performing a specific service such as a personal computer, a portable terminal or the like, as well as a data processing device that can be generally accessed by a client through a network, may be defined as a server.

Figure 3:
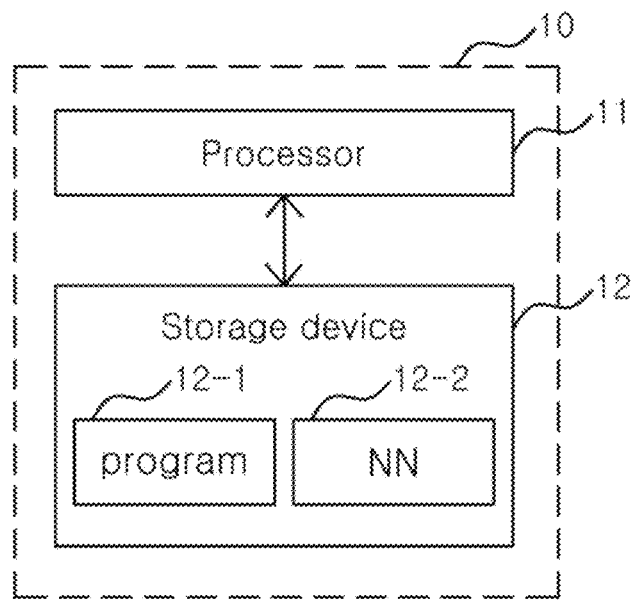
FIG. 3 is a view showing a hardware configuration of a disease diagnosis system using multiple color models and a neural network according to an embodiment.

The server 10 may include a processor 11 and a storage device 12 as shown in FIG. 3. The processor 11 may correspond to a computing device capable of driving a program 12-1 for implementing one or more embodiments of the invention, and the processor 11 may perform diagnosis using the program 12-1 and a neural network 12-2 defined by one or more embodiments of the invention. The neural network 12-2 may include a patch neural network that performs patch-level diagnosis as described below. The patch neural network may perform patch-level diagnosis using multiple color models.

When it is described that diagnosis is performed using multiple color models, it may signify that whether a disease exists is diagnosed by receiving a channel value (or channel values) of each of a plurality of color models different from each other for an input layer. When a first color model to a K-th color model, which are K color models (where K is an integer equal to or greater than 2), are used, the patch neural network may receive channel values respectively corresponding to the first color model to the K-th color model for the input layer. For example, when an RGB color model, an HSV color model, and a gray color model are used, the patch neural network may receive RGB three channels, an HSV channel, and a gray channel.

For the patch-level diagnosis using multiple color models according to an embodiment of the invention, at least some of an RGB model, an HSV model, a CMYK model, a YCbCr model, and a Gray model may be used.

According to implementation examples, the neural network 12-2 may further include a neural network that performs slide-level diagnosis. According to embodiments, the configuration of performing the slide-level diagnosis may be implemented through various machine learning techniques as well as the neural network. According to one or more embodiments of the invention, the known XGBoost is used as a diagnosis engine for performing the slide-level diagnosis. However, diagnosis engines according to various types of machine learning techniques may be implemented, and it goes without saying that such diagnosis engines may be stored in the storage unit 12.

The server 10 may include a processor 11 and a storage device 12 as shown in FIG. 3. The processor 11 may correspond to a computing device capable of driving a program 12-1 for implementing one or more embodiments of the invention, and the processor 11 may perform diagnosis using the program 12-1 and a neural network 12-2 defined by one or more embodiments of the invention. The neural network 12-2 may include a patch neural network that performs patch-level diagnosis as described below. According to implementation examples, the neural network 12-2 may further include a neural network that performs slide-level diagnosis. According to embodiments, the configuration of performing the slide-level diagnosis may be implemented through various machine learning techniques as well as the neural network. According to one or more embodiments of the invention, the known XGBoost is used as a diagnosis engine for performing the slide-level diagnosis. However, diagnosis engines according to various types of machine learning techniques may be implemented, and it goes without saying that such diagnosis engines may be stored in the storage unit 12.

The storage device 12 may corresponds to a data storage unit capable of storing the program 12-1, the neural network 12-2, and/or a diagnosis engine for performing the slide-level diagnosis, and may be implemented as a plurality of storage units according to implementation examples. In addition, the storage device 12 may correspond to a temporary storage device or a memory that may be included in the processor 11, as well as a main memory device or the like included in the server 10.

Although it is shown in FIG. 1 or 3 that the diagnosis system 100 is implemented as any one physical device, those skilled in the art may easily infer that the diagnosis system 100 according to one or more embodiments of the invention may be implemented by organically combining a plurality of physical devices as needed.

In the description of the embodiments as provided herein, when it is described that the diagnosis system 100 performs diagnosis, it may denote a series of processes receiving a biometric image expressing a biological tissue, i.e., the entire slide or a patch that is a part of the slide, and outputting an output data defined in this specification.

According to an example, the diagnosis system 100 may perform two-phase diagnosis. The first phase may be a process of performing patch-level diagnosis, and in this process, the diagnosis system 100 may receive input for each patch of the slide and output whether or not a disease is expressed in a corresponding patch. It goes without saying that a neural network for this purpose may be implemented by learning.

The second phase may output whether a disease is expressed in the slide through the diagnosis result of the first phase. For this process, a neural network or a predetermined machine learning technique may be used.

That is, although it is determined that a disease is expressed in some patches according to the diagnosis result of each patch, there may be a possibility that a disease is not determined as being expressed in a biological tissue corresponding to the entire slide including a corresponding patch. For example, a case in which patches determined to have a disease are sparsely scattered in the slide or the number of the patches is small, or physical characteristics such as density or the like (e.g., location, size, density, etc.) of patches determined to have a disease may have an important meaning in actually determining whether a disease is expressed in a corresponding slide. Therefore, the second phase may perform effective and highly accurate diagnosis by determining whether a disease is expressed in the slide on the basis of the diagnosis result for each patch and the characteristics of the patches determined on the basis of the diagnosis result (i.e., patches diagnosed as expressing a disease).

Meanwhile, according to one or more embodiments of the invention, the neural network performing the patch-level diagnosis may perform diagnosis by further considering surrounding patches of a corresponding patch, rather than performing diagnosis using only the corresponding patch. Such neural network performing like this has been disclosed in detail in the Korean patent application filed by the applicant of the present invention (application number 10-2016-0168176, a system and method for diagnosing disease using a neural network, hereinafter referred to as 'previous application'). Through the previous application, accuracy of diagnosis may be improved when the surrounding areas are considered together, rather than when the diagnosis is performed considering only a very narrow area, i.e., an area corresponding to the patch. Furthermore, according to one or more embodiments of the invention, there is an effect of more accurately determining whether a disease exists in the slide by further considering physical characteristics such as the location, density, and cluster size of patches in the entire slide, in addition to those of surrounding patches of a specific patch. The previous application is included as a reference of the present invention, and contents thereof may be regarded as being described in this specification.

Figure 5A:
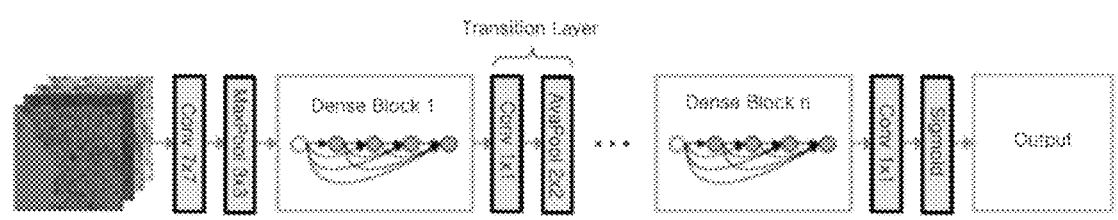
FIGS. 5A and 5B are views showing an exemplary configuration of a neural network according to another embodiment.
Figure 5B:
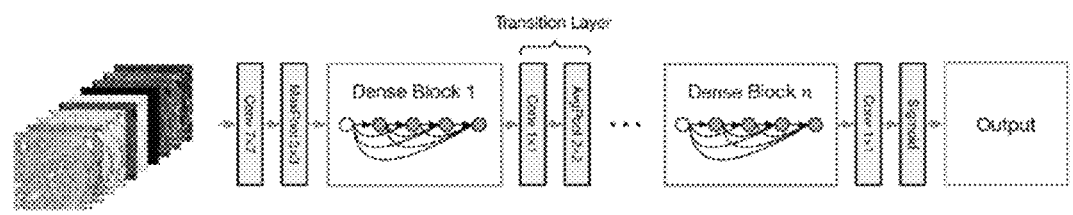

Of course, according to another embodiment of the invention, a single one-way neural network may be used instead of a micro network and a macro network, i.e., a two-way neural network, like the previous application. For example, the neural network according to an embodiment of the invention may be as shown in FIGS. 5A and 5B.

In any case, the neural network is sufficient if it is a neural network defined to receive a patch and output whether a disease is expressed in the input patch.

At this point, the neural network is trained to receive each channel value of a plurality of color models corresponding to each patch as an input value and perform diagnosis.

When a first color model to a K-th color model, which are K color models (K is an integer equal to or greater than 2), are used, the neural network may be trained to receive an input value of a channel value (or channel values) corresponding to each of the first color model to the K-th color model and perform diagnosis. In other words, for each patch, the neural network is trained to receive first image information to K-th image information corresponding to the patch for an input layer, and output a patch-level diagnosis result indicating whether a disease exists in the patch, and at this point, the i-th image information (i is an arbitrary integer of $1 \leq i \leq K$) is configured of at least one channel value corresponding to the i-th color model.

Meanwhile, the state information output by the neural network performing the patch-level diagnosis may be information indicating a probability of whether a specific disease (e.g., cancer of a specific type) is expressed in a tissue corresponding to the patch. When a probability of greater than or equal to a specific reference value (threshold value) appears, the neural network may determine the patch as a patch in which a disease (e.g., prostate cancer) is expressed.

Of course, the neural network may provide information indicating a degree of progression of a specific disease (or a probability corresponding to the degree of progression), as well as whether or not a specific disease is expressed, as disclosed in the previous application. For example, when one or more embodiments of the invention are used for diagnosis of prostate cancer, the Gleason Pattern or Gleason Score, which are indexes indicating a degree of progression of prostate cancer, may be included in the state information output from the neural network, which is an index. For example, the Gleason score has a value of 2 to 5, and a larger number indicates a higher degree of expression of the prostate cancer. Accordingly, the state information may denote a probability that a biological tissue corresponding to a patch to be diagnosed corresponds to a specific value (e.g., 3, 4 or 5) of the Gleason score.

There may be a plurality of state information that are used in one or more embodiments. For example, first state information may indicate a probability of the Gleason score for being 3, second state information may indicate a probability of the Gleason score for being 4, and third state information may indicate a probability of the Gleason score for being 5, and all state channels corresponding to the first state information, the second state information, and the third state information may be defined in an output layer. According to implementations, state information indicating a probability that the Gleason score has a predetermined range (e.g., 3 to 5, 4 to 5, etc.) may be defined. That is, one piece of state information may correspond to a plurality of indexes expressing a progress state of a disease.

In this case, the neural network may determine that the patch is a disease patch, i.e., a disease-expressed patch, when the state information having a Gleason score of 3 or more is equal to or greater than a predetermined threshold value.

Meanwhile, the threshold value used by the neural network may be set variously. According to embodiments, a plurality of threshold values may be used. It goes without saying that a specific patch may be determined as a disease-expressed patch, i.e., a disease patch, or a normal patch according to the threshold value.

According to one or more embodiments of the invention, there may be a plurality of threshold values used by the neural network, and in this case, a disease patch diagnosed according to each of the plurality of threshold values may vary. Therefore, the characteristic of the disease patch arranged in the slide may also vary according to each of the threshold values. Therefore, when a certain threshold value is used, the accuracy of the diagnosis result of the slide may also vary.

Accordingly, one or more embodiments of the invention may be implemented to allow the slide diagnosis engine to perform diagnosis of the slide by diversely considering physical characteristics that the disease patches diagnosed according to each of the plurality of threshold values have in the slide as described below. One or more embodiments like this will be described below.

When the diagnosis system 100 is implemented to be included in a predetermined server 10, the diagnosis system 100 may perform communication with at least one client (e.g., 20-1) accessible to the server 10. In this case, the client (e.g., 20, 20-1) may transmit a biometric image to the diagnosis system 100, and the diagnosis system 100 may perform diagnosis on the transmitted biometric image according to one or more embodiments of the invention. In addition, the diagnosis system 100 may transmit a diagnosis result to the client (e.g., 20, 20-1).

The diagnosis system 100 may perform patch-level diagnosis using a neural network according to one or more embodiments of the invention. Of course, a process of training the neural network may be performed first to perform the diagnosis. It goes without saying that the multiple color models described above may be used in the process of training the neural network.

In addition, a predetermined neural network may also be used for the slide-level diagnosis as described above.

Accordingly, the diagnosis system 100 may be a system that receives a neural network trained according to one or more embodiments of the invention and a program for performing diagnosis using the neural network from the outside and performs diagnosis, or it may be a system that performs even the training. In addition, the diagnosis system 100 may be implemented as a dedicated device manufactured to implement one or more embodiments of the invention, not a general-purpose data processing device. In this case, a component for scanning biometric images may be further provided.

As disclosed in the previous application, the neural network may have a characteristic of performing diagnosis on a specific patch considering not only an image of the specific patch itself to perform diagnosis on the specific patch, but also considering even an image of at least one adjacent patch of the specific patch. Through a system like this, there is an effect of improving accuracy to a very meaningful level in diagnosing a disease that should consider not only the biological tissue but also the state of surrounding tissues of the biological tissue to actually diagnose a biological tissue corresponding to a specific patch. In addition, when a biometric image is divided into a plurality of patches, there is a strong effect on the influence of a diagnosis result that may occur depending on the method of dividing patches or the location of a divided area in the biological tissue.

Of course, as described above, the neural network may not have the features disclosed in the previous application, and in any case, the neural network may be a neural network that is trained to perform diagnosis for each patch.

At this point, unlike what is described in the previous application, the neural network may receive a channel value of each of multiple color models for each of the pixels included in the patch as an input value. That is, the neural network may further receive a channel value (or channel values) defined by each of one or more additional color models, in addition to the values of original channels defined by the original color model of the patch. For example, the neural network may further receive each channel value of the additional color models (e.g., a gray channel value, HSV 3 channel values, CMYK 4 channel values and/or YCbCr 3 channel values, etc.) as an input, together with each channel value of the original color model of the pixels included in the patch, while receiving an input for each patch.

In this case, it may have a strong effect when the color of a biometric image changes due to a factor (e.g., characteristics of a diagnosis institution, dyeing reagent, etc.) unrelated to image features related to a disease. In addition, as a single image is expressed in multiple color models and all of the color models are used, there is an advantage in that such important information may be reflected more sufficiently when image features related to a disease are reflected and displayed.

Figure 2:
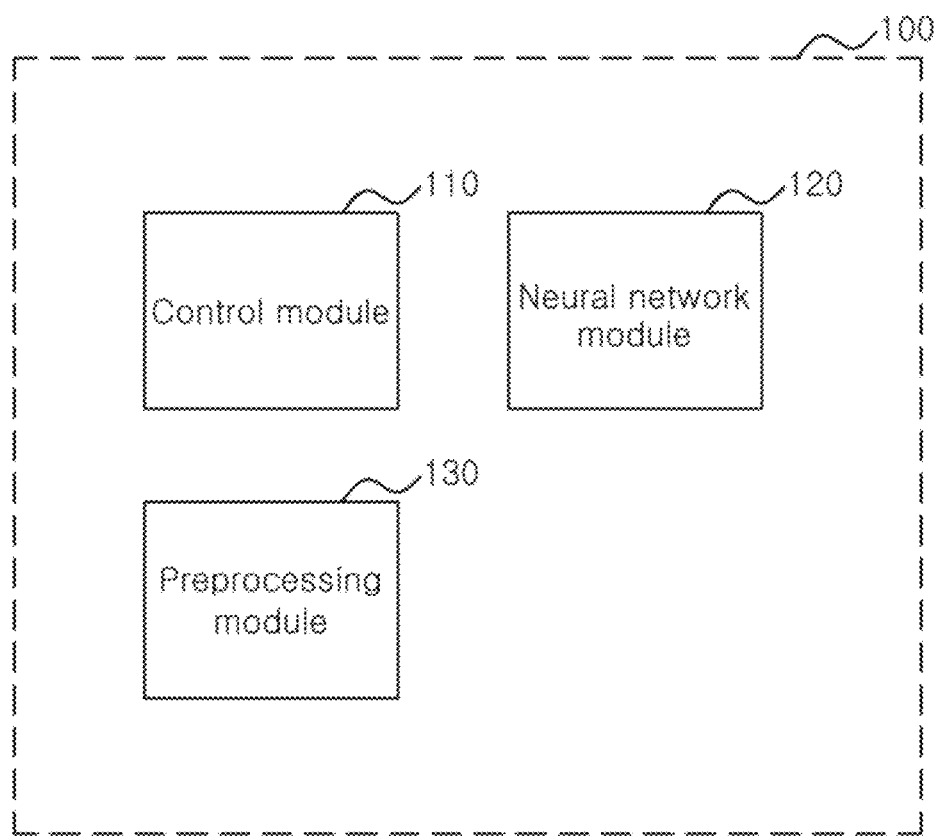
FIG. 2 is a view showing a logical configuration of a disease diagnosis system using multiple color models and a neural network according to an embodiment.

The diagnosis system 100 for implementing one or more embodiments may have a configuration logically the same as shown in FIG. 2.

FIG. 2 is a view showing a logical configuration of a disease diagnosis system using multiple color models and a neural network according to an embodiment of the invention.

Referring to FIG. 2, the diagnosis system 100 includes a control module 110, and an analysis module 120 storing the neural network and/or slide diagnosis engine. In addition, the diagnosis system 100 may further include a preprocessing module 130. According to embodiments of the invention, some components among the components described above may not necessarily correspond to the components essential to implementation of the invention, and in addition, it goes without saying that the diagnosis system 100 may include more components according to embodiments. For example, the diagnosis system 100 may further include a communication module (not shown) for communicating with the client (e.g., 20, 20-1).

The diagnosis system 100 may denote a logical configuration provided with hardware resources and/or software needed to implement one or more embodiments of the invention, and does not necessarily mean a physical component or a device. That is, the diagnosis system 100 may mean a logical combination of hardware and/or software provided to implement one or more embodiments of the invention, and may be implemented as a set of logical components if needed by being installed in the devices separated from each other and performing their functions to implement one or more embodiments of the invention. In addition, the diagnosis system 100 may denote a set of components separately implemented for each function or role for implementing one or more embodiments of the invention. For example, the control module 110, the analysis module 120, and/or the preprocessing module 130 may be located in different physical devices, or may be located in the same physical device. In addition, according to implementation examples, combinations of software and/or hardware configuring each of the control module 110, the analysis module 120, and/or the preprocessing module 130 may also be located in different physical devices, and components located in different physical devices may be organically combined with each other to implement each of the modules.

In addition, in this specification, a module may denote a functional or structural combination of hardware for performing one or more embodiments of the invention and software for driving the hardware. For example, those skilled in the art may easily infer that the module may denote a predetermined code and a logical unit of hardware resources for executing the predetermined code, and does not necessarily denote a physically connected code or a single type of hardware.

The control module 110 may control other components (e.g., the diagnosis module 120 and/or the preprocessing module 130) included in the diagnosis system 100 in order to implement one or more embodiments of the invention.

In addition, the control module 110 may perform diagnosis according to one or more embodiments of the invention by using the neural network and/or the slide diagnosis engine stored in the diagnosis module 120.

The diagnosis module 120 may include a patch diagnosis engine for performing patch-level diagnosis and a slide diagnosis engine for performing slide-level diagnosis.

As described above, the patch-level diagnosis engine may be implemented through a deep learning-based neural network according to one or more embodiments of the invention. As the slide diagnosis engine, the deep learning-based neural network may be used, or a predetermined machine learning (e.g., XGBoost) engine, other than the neural network, may be used.

The neural network may denote a set of information expressing a series of design items defining the neural network. In this specification, the neural network may be a convolution neural network.

As is well in the art, the convolution neural network may include an input layer, a plurality of hidden layers, and an output layer. Each of the plurality of hidden layers may include a convolution layer and a pooling layer (or subsampling layer).

The convolution neural network may be defined by functions, filters, strides, weighting factors or the like for defining each of these layers. In addition, the output layer may be defined as a fully connected feedforward layer.

The design details of each layer constituting the convolution neural network are widely known in the art. For example, known functions or functions separately defined to implement one or more embodiments of the invention may be used for the number of layers to be included in the plurality of layers and for each of a convolution function, a pooling function, and an activation function for defining the plurality of layers.

According to an embodiment of the invention, the neural network performing patch-level diagnosis uses a known densenet, and at this point, it may be designed to consider neighboring patches, as well as a specific patch to be diagnosed, as is disclosed in the previous application. In addition, various neural networks may be used, and in any case, the neural network may be defined to receive a specific patch as an input and output a feature value corresponding to a disease occurrence probability of the specific patch.

The control module 110 may receive input data, i.e., input for each patch, for the patch-level neural network, i.e., a trained neural network, stored in the diagnosis module 120. At this point, the control module 110 may receive a channel value corresponding to each of the multiple color models for each patch as described above.

More specifically, the patch-level neural network may receive the first image information to the K-th image information corresponding to each patch for the input layer, and the i-th image information (i is an arbitrary integer of $1 \leq i \leq K$) is configured of at least one channel value corresponding to the i-th color model.

For example, in the case of an embodiment using an RGB color model, an HSV color model, and a CMYK color model, the patch-level neural network may receive RGB 3 channel values corresponding to a corresponding patch, i.e., first image information, HSV 3 channel values corresponding to a corresponding patch, i.e., second image information, and CMYK 4 channel values corresponding to a corresponding patch, i.e., third image information, for each patch.

It goes without saying that each received channel value of a plurality of color models may be obtained by converting the original pixel value of each patch into each color model.

In addition, output data, i.e., a feature value corresponding to a disease occurrence probability corresponding to a patch, may be output by performing operations defined by the neural network. In addition, according to embodiments, whether or not a disease is expressed in a corresponding patch may be output according to whether the feature value is a predetermined threshold value, for the slide-level diagnosis as described below.

In addition, the diagnosis module 120 may include a slide diagnosis engine, and the slide diagnosis engine may also be trained and implemented by the control module 110.

The slide diagnosis engine may mark a disease patch according to an output result of the neural network. Marking may denote identifying disease patches within a slide. According to an example, the slide diagnosis engine may generate a heatmap by displaying disease patches to be distinguished from the other patches. In addition, the disease patches may be clustered in plurality on the basis of the generated heatmap. According to an embodiment, the slide diagnosis engine may cluster the disease patches into at least two clusters. Then, two largest clusters among them may be used for slide diagnosis. However, it goes without saying that two or more clusters may be used for slide diagnosis.

The slide diagnosis engine may calculate a predetermined feature value for each cluster. Then, the slide diagnosis engine is trained to output whether a disease is expressed in a slide corresponding to the input data by using the calculated feature value as an input data.

In addition, the slide diagnosis engine may be trained considering all the plurality of threshold values. Through this, a slide diagnosis result that is robust to setting of a threshold value may be output. This will be described below.

The preprocessing module 130 may perform needed preprocessing on a biometric image before performing diagnosis using a neural network. For example, the preprocessing on the biometric image may include a process of patching the biometric image into patches of a predefined size.

In addition, according to embodiments, the preprocessing module 130 may calculate a channel value corresponding to each color model by converting pixels of each patch into multiple color models. That is, the preprocessing module 130 may generate first image information to K-th image information (here, K is an integer equal to or greater than 2) corresponding to a patch. At this point, the i-th image information (i is an arbitrary integer of 1<=i<=K) is configured of at least one channel value corresponding to the i-th color model. For example, in the case of an embodiment using an RGB color model, an HSV color model, and a CMYK color model, when the original pixel of a patch is configured of RGB 3 channel values, the preprocessing module 130 may convert the original RGB 3 channel values of each pixel of a corresponding patch into HSV 3 channel values and CMYK 4 channel values.

In addition, those skilled in the art may easily infer that the preprocessing module 130 may perform appropriate image processing as needed in a way suitable for the neural network.

Figure 4A:
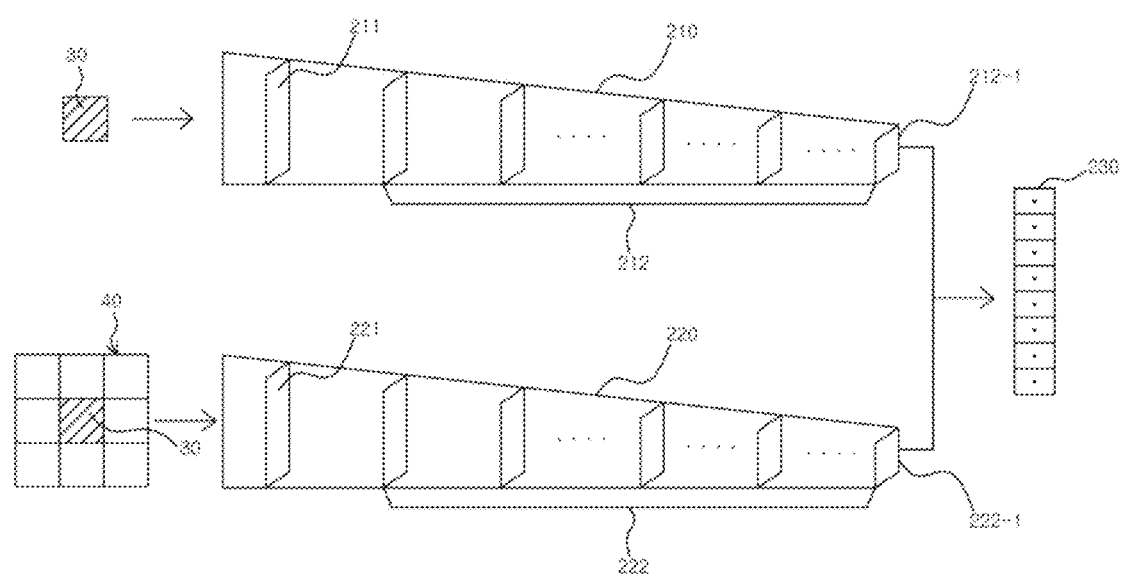
FIGS. 4A and 4B are views showing an exemplary configuration of a neural network according to an embodiment.
Figure 4B:
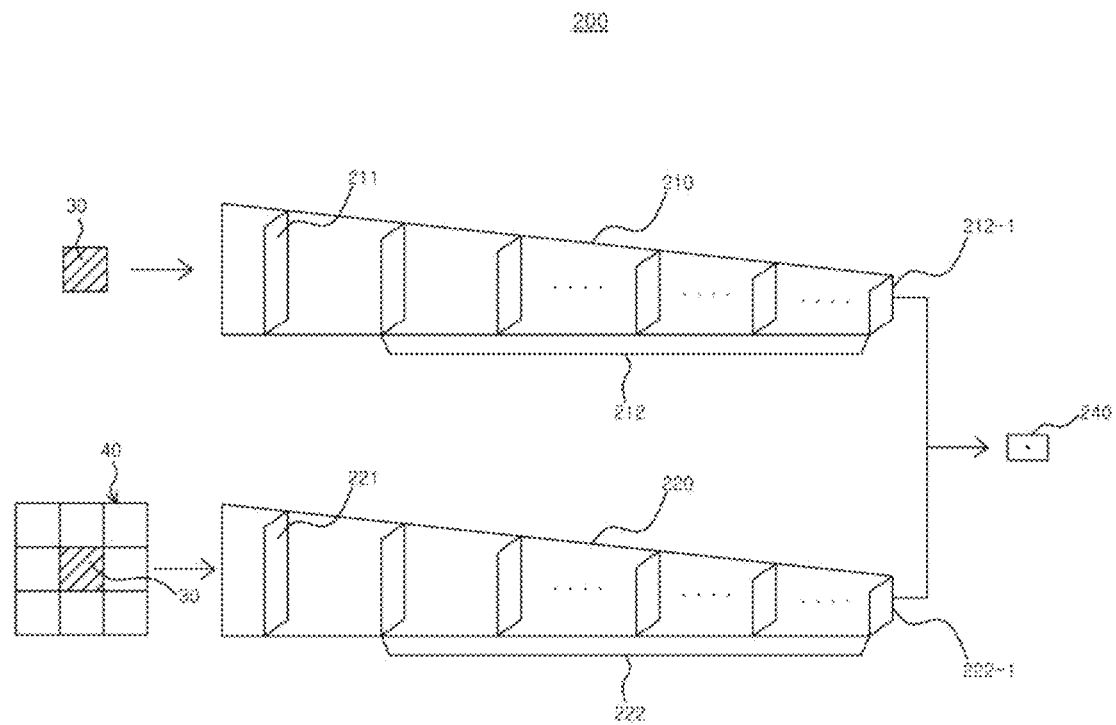

FIGS. 4A and 4B are views showing the configuration of a neural network according to an embodiment of the invention.

Referring to FIGS. 4A and 4B, a neural network 200 according to one or more embodiments of the invention includes a micro neural network and a macro neural network.

Referring to FIG. 4A first, as disclosed in the previous application, the micro neural network includes a plurality of layers 210 and an output layer 230. The plurality of layers 210 include an input layer 211 and a plurality of hidden layers 212.

The macro neural network includes a plurality of layers 220 and an output layer 230. The plurality of layers 220 includes an input layer 221 and a plurality of hidden layers 222.

The micro neural network is defined to receive a specific patch 30 and output a diagnosis result of the specific patch, i.e., output data defined in the output layer 230.

In addition, the macro neural network is defined to receive a macro patch 40 including the specific patch 30 and at least one adjacent patch of the specific patch 30, and output a diagnosis result of the specific patch.

That is, the neural network 200 according to one or more embodiments of the invention may output a diagnosis result considering even the image features of adjacent patches of the specific patch 30, in addition to the image features of the specific patch 30, in order to output the diagnosis result of the specific patch 30.

Although the macro patch 40 in FIGS. 4A and 4B shows an example of using 3×3 patches surrounding a patch, it goes without saying that various embodiments are possible.

The output layer 230 may receive output data of each of a first immediate-before layer 212-1, which is a layer immediately before the output layer 230 included in the micro neural network, and a second immediate-before layer 222-1, which is a layer immediately before the output layer 230 included in the macro neural network, and output an output data defined in the output layer 230. The first immediate-before layer 212-1, the second immediate-before layer 222-1, and the output layer 230 may be fully connected.

As a feedforward function defining the output layer 230, any one among various functions that output an output data through the output layer 230 as a result of an input data input for the input layer and passing through the neural network 200 may be used.

As a result, in order to perform diagnosis on the specific patch 30, the neural network 200 is trained to output an output data of the output layer 230 corresponding to annotation values of a plurality of training data, considering both the image features of the specific patch 30 and the image features of the macro patch 40 including the specific patch 30.

That is, a plurality of training data is used to train the neural network 200, and the plurality of training data may include a pair of a specific patch 30 and a macro patch 40. In addition, the macro patch 40 may also perform learning by using annotation information of the specific patch 30.

Then, the neural network 200 will be trained to output an output data corresponding to the annotation information of the specific patch 30 considering both the image features of the specific patch 30 and the macro patch 40.

Then, when the trained neural network 200 receives a target patch to be diagnosed and a macro patch corresponding to the target patch as input data of the micro neural network and the macro neural network, it may output a diagnosis result of the target patch, i.e., output data of the output layer 230.

As shown in FIG. 4A, the output layer 230 may output a diagnosis result of the specific patch 30 to be diagnosed as an output data. The diagnosis result may include at least information on the state of a disease of the specific patch 30. The information on the state of a disease may simply denote information on whether a specific disease is expressed in a specific patch 30 (or a probability value). However, depending on the type of a disease, the information on the state of a disease may include information indicating a degree of progression of the disease more specifically.

As disclosed in the previous application, the output layer may be designed to output various additional information, in addition to simply outputting whether or not a disease is expressed. For example, it may include information indicating a degree of progression of a disease and/or related factor information indicating a degree of expression of a related factor related to the value of the state channel. Since this is disclosed in detail in the previous application, detailed description thereof will be omitted for sake of brevity.

When the neural network 200 shown in FIG. 4A is used, although not shown in FIG. 4a, it goes without saying that there may be a layer that receives the output data of the output layer 230 and outputs a feature value corresponding to the probability of expressing a disease of a finally input patch.

Alternatively, as shown in FIG. 4B, the neural network may be designed to have a layer 240 for outputting a feature value corresponding to the probability of expressing a disease of the input patch in substitution for the layer that outputs a plurality of state channels and a related factor channel as shown in FIG. 4A.

According to another embodiment of the invention, the neural network for patch-level diagnosis may be designed to have a single path rather than a method having two paths (paths of a micro network and a macro network) as shown in FIGS. 4A and 4B. This example may be as shown in FIGS. 5A and 5B.

FIGS. 5A and 5B are views showing an exemplary configuration of a neural network according to another embodiment of the invention.

Referring to FIGS. 5A and 5B, as described above, a neural network may be defined to receive an input by the patch and determine whether a disease is expressed in the input patch. At this point, the neural network may receive each channel value of the multiple color models. As shown in FIG. 5A, the neural network may receive original RGB 3 channels and a gray channel (a total of 4 channels). Alternatively, as shown in FIG. 5B, the neural network may receive RGB 3 channels, HSV 3 channels, and CMYK 4 channels (a total of 10 channels). It goes without saying that it is possible to combine various color models.

As shown in FIGS. 5A and 5B, input data may be defined to pass through a convolution layer and a plurality of layers per maxpooling and to output an output data, i.e., whether the input patch is a disease patch. Such a neural network may be a neural network using a known densenet model. In addition, at this point, it can be seen that compared with the original densenet model, 1×1 convolution is added to the neural network according to the spirit of the present invention, and there is an effect of confirming an internal feature map. In addition, although a sigmoid function is used as an activation function, various activation functions may be used.

Those skilled in the art may easily infer that a neural network that performs patch-level diagnosis in various other ways may be defined.

Figures 6, 7:
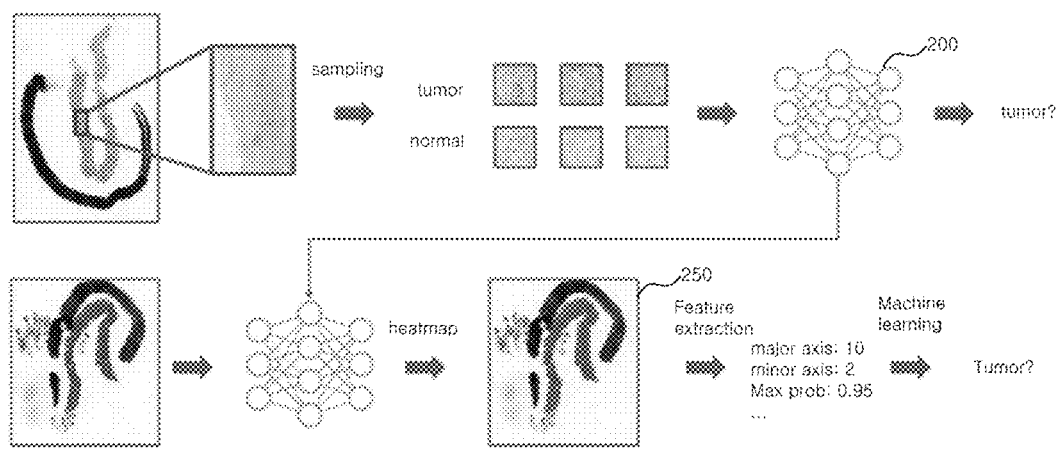
FIG. 6 is a view for explaining the concept of a two-phase disease diagnosis method according to an embodiment.
FIG. 7 is a view showing an experiment result of a patch-level diagnosis method according to an embodiment.

FIG. 7 is a view showing an experiment result of a patch-level diagnosis method according to an embodiment of the invention. In the experiment of FIG. 7, a neural network capable of additionally receiving a gray channel value, in addition to the original 3 channels of each pixel value, is applied.

Referring to FIG. 7, the neural network has trained using 62,358 patches labeled as cancer and 108,300 patches labeled as normal as a train data set, and 8,963 cancer patches and normal patches are used as a validation set. In addition, 14,898 cancer patches and 19,089 normal patches are used as a test set.

Then, it is known that each of the accuracy, precision, sensitivity, and specificity, which are experiment results at that time, demonstrates very high performance as shown in FIG. 7. In addition, it is confirmed that performance is improved compared with a case of using only 3 channels of the original value as the pixel value.

FIG. 6 is a view for explaining the concept of a two-phase disease diagnosis method according to an embodiment of the invention.

As shown in FIG. 6, a biometric image corresponding to a biological tissue, i.e., patches sampled from a slide, may be used for training of the neural network 200. The patches may be sampled so that patches labeled as cancer and patches labeled as normal have a predetermined ratio.

The neural network 200 is trained by receiving input data for each patch further including a gray channel as described above, and as a result, the neural network 200 is trained to output whether each of the patches is cancer (or a probability value).

Then, the neural network 200 trained like this may perform patch-level diagnosis on each patch included in each slide when the slide is input as shown in the lower part of FIG. 6.

In addition, the slide diagnosis engine may mark disease patches according to a patch-level diagnosis result. For example, a heatmap may be generated as shown in FIG. 6.

Figure 8A:
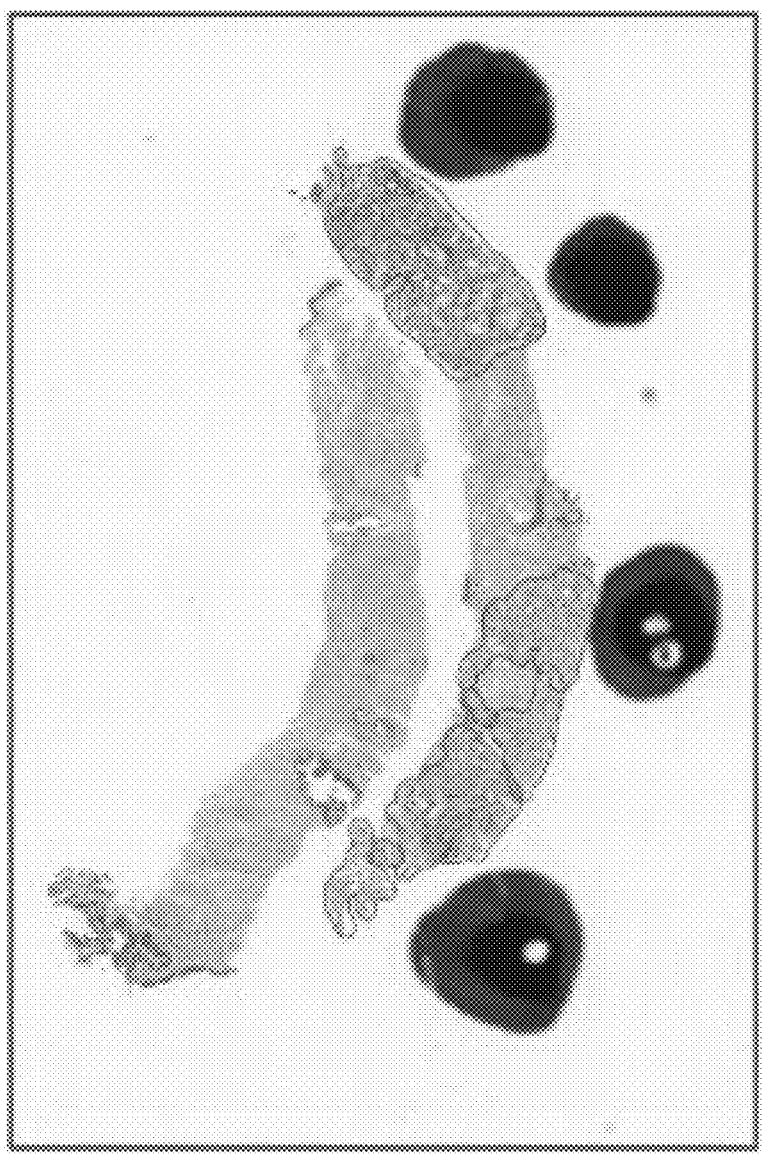
FIGS. 8A and 8B are views showing a marking result based on a patch-level diagnosis result according to an embodiment.
Figures 8B, 9:
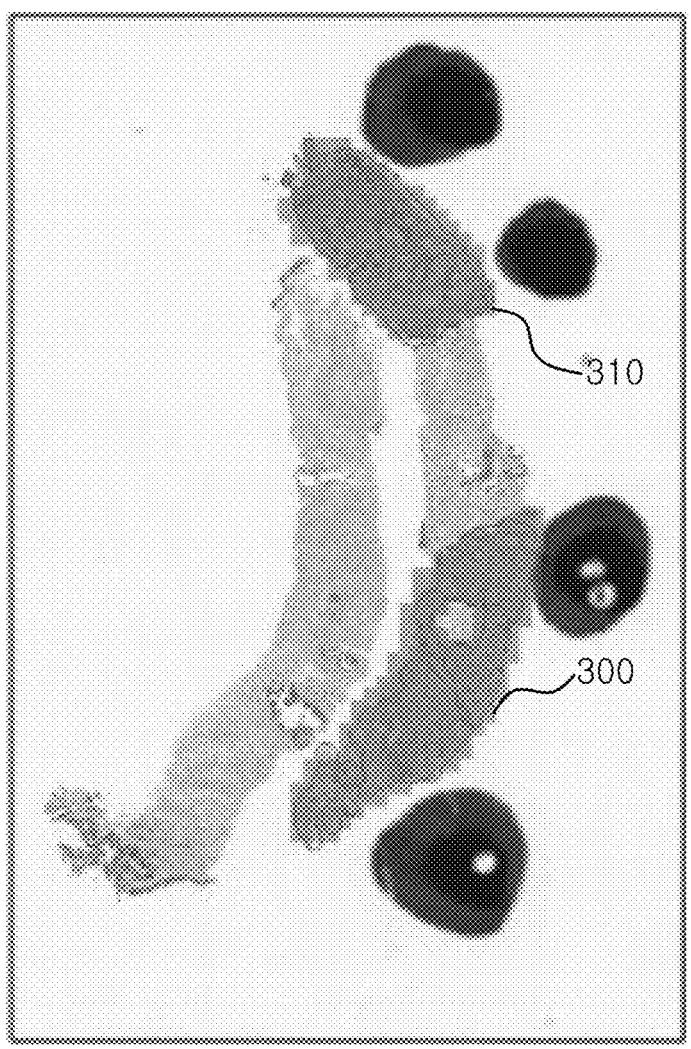
FIG. 9 is a view showing an experiment result of a slide-level diagnosis method according to an embodiment.

In addition, FIGS. 8A and 8B are views showing a marking result based on a patch-level diagnosis result according to an embodiment of the invention. FIG. 8A shows an image of a biological tissue labeled by a skilled expert, and FIG. 8B shows a heatmap generated by the trained neural network 200. As is known from FIGS. 8A and 8B, it can be seen that a very accurate diagnosis can be made.

Meanwhile, the slide diagnosis engine may generate a cluster according to the generated heatmap. The slide diagnosis engine may cluster disease patches using a predetermined clustering algorithm. According to an embodiment of the present invention, although the slide diagnosis engine performs clustering through a known DBSCAN algorithm, it goes without saying that various clustering techniques may be used.

The slide diagnosis engine may extract cluster features for each cluster generated as a result of clustering.

The cluster feature may be a characteristic value capable of expressing a characteristic associated with expression of a disease.

According to an example, the cluster feature may include the number of disease patches included in the cluster, an average probability value of disease for each patch, a maximum probability value of disease for each patch, and a minimum probability value of disease for each patch. It can be confirmed that when these cluster features are included, the diagnostic result of the slide diagnosis engine is relatively improved.

Also, according to embodiments, the cluster feature may further include a major axis, a minor axis, an area, and a density of each cluster. This is closely related to the physical characteristics of the cluster, and when such cluster features are used together, diagnosis performance may be further improved.

Meanwhile, the clusters may have different locations, sizes, and cluster features as described above according to whether or not each patch is determined as a disease patch. In addition, it depends on the threshold value used for patch-level diagnosis.

According to one or more embodiments of the invention, a plurality of threshold values may be used together for slide-level diagnosis.

According to an example, although five different threshold values are used in an embodiment of the invention, various embodiments are possible.

In addition, it goes without saying that the result of diagnosing a specific patch as a disease patch may vary according to each of the threshold values, and the clustering result may vary accordingly.

The slide diagnosis engine according to an embodiment of the present invention forms M (e.g., 2) clusters by clustering, for example, N (e.g., 5) threshold values and patches expressing a disease based on each of the N threshold values in a predetermined manner.

Then, P cluster features (e.g., 8 cluster features described above) are calculated for each of the formed clusters. In this case, M×N×P (e.g., 80) cluster features may be extracted for one slide.

In addition, the slide diagnosis engine may be trained to input these feature values as input values and output whether the slide has a disease as an output data.

An experiment result of this embodiment is shown in FIG. 9.

FIG. 9 is a view showing an experiment result of a slide-level diagnosis method according to an embodiment of the invention.

The experiment result shown in FIG. 9 is a case using all the eight cluster features described above, which shows a result of an experiment that uses five threshold values and two clusters. In this embodiment, 478 slides expressing cancer and 218 normal slides are used as a train data set. In addition, 117 slides expressing cancer and 57 normal slides are used as a validation set, and 1,302 slides expressing cancer and 1,658 normal slides are used as a test set.

Then, it is known that the accuracy, precision, sensitivity, and specificity, which are the experiment results at that time, show high performance as shown in FIG. 9, respectively.

In addition, although an example of applying one or more embodiments of the invention to detected prostate cancer has been mainly described in this specification, those skilled in the art may easily infer that accurate diagnosis is possible when the one or more embodiments the invention are applied to other diseases that need diagnosis to be performed on a specific tissue considering the state of surrounding tissues of the tissue, as well as the specific tissue.

Meanwhile, according to implementation examples, the diagnosis system 100 may include a processor and a memory for storing programs executed by the processor. The processor may include single-core CPUs or multi-core CPUs. The memory may include high-speed random-access memory and may include one or more non-volatile memory devices such as magnetic disk storage devices, flash memory devices, and other non-volatile solid state memory devices. Access to the memory by the processor and other components may be controlled by a memory controller.

Meanwhile, the diagnosis method through multiple color models and a neural network according to an embodiment of the present invention may be implemented in the form of a computer-readable program command and stored in a computer-readable recording medium, and control programs and target programs according to an embodiment of the present invention may also be stored in the computer-readable recording medium. The computer-readable recording medium includes all types of recording devices for storing data that can be read by a computer system.

The program commands recorded in the recording medium may be specially designed and configured for the present invention, or may be known to and used by those skilled in the software field.

One or more embodiments of the invention may be used in a system and method for diagnosing a disease using multiple color models and a neural network.

Examples of the computer-readable recording medium include magnetic media such as hard disks, floppy disks, and magnetic tapes, optical media such as CD-ROMs and DVDs, magneto-optical media such as floptical disks, and hardware devices specially configured to store and execute program commands, such as ROM, RAM, flash memory and the like. In addition, the computer-readable recording medium may be distributed in computer systems connected through a network to store and execute computer-readable codes in a distributed manner.

Examples of program instructions include high-level language codes that can be executed by a device that electronically processes information using an interpreter or the like, e.g., a computer, as well as machine language codes such as those produced by a compiler.

The hardware device described above may be configured to execute as one or more software modules to perform the operation of the present invention, and vice versa.

The above description of the present invention is for illustrative purposes, and those skilled in the art may understand that it is possible to easily transform into other specific forms without changing the spirit or essential features of the present invention. Therefore, it should be understood that the embodiments described above are illustrative and non-limiting in all respects. For example, each component described as a single form may be implemented in a distributed manner, and in the same manner, components described as being distributed may also be implemented in a combined form.

The scope of the present invention is indicated by the claims described below rather than the detailed description, and the meaning and scope of the claims and all changes or modified forms derived from the equivalent concepts thereof should be interpreted as being included in the scope of the present invention.

The invention claimed is:

1. A disease diagnosis system implemented in a system including a processor and a storage device storing a neural network, and using a slide of which biological tissue is disposed thereon and of which a biometric image is obtained therefrom, and the neural network, the system comprising:
   a preprocessing module configured to generate, for each of a plurality of patches generated by dividing the biometric image obtained from the slide in a predetermined size, first image information to K-th image information, wherein, K is an integer equal to or greater than 2, corresponding to the patch, wherein i-th image information, i being an arbitrary integer in the range of $1<=i<=K$, and that is configured of at least one channel value corresponding to an i-th color model, and in which all of a first color model to a K-th color model are different color models; and
   a patch neural network configured to receive, for each of the plurality of patches, the first image information to the K-th image information corresponding to the patch through an input layer, and outputting a patch-level diagnosis result indicating whether a disease exists in the corresponding patch.

2. The system according to claim 1, wherein each of the first color model to the K-th color model is any one among a Red/Green/Blue (RGB) model, a Hue/Saturation/Blackness-Value (HSV) model, a Cyan-Magenta-Yellow-Black (CMYK) model, a Luma/Blue-Difference/Red-Difference (YCbCr) model, and a Gray model.

3. The system according to claim 1, further comprising a slide diagnosis engine configured to mark a patch determined as cancer as a result of patch-level diagnosis on each of the plurality of patches included in the slide, and to output a slide-level diagnosis result indicating whether a disease exists in the slide on the basis of the marked result.

4. The system according to claim 3, wherein the slide diagnosis engine forms a plurality of clusters by clustering the patches determined as cancer in a predetermined manner, receives a plurality of cluster features as input values for each of the formed clusters, and outputs the slide-level diagnosis result of the slide including the clusters.

5. The system according to claim 1, wherein the disease is prostate cancer.

6. A disease diagnosis system implemented in a system including a processor and a storage device storing a neural network, and using a slide of which biological tissue is disposed thereon and of which a biometric image is obtained therefrom, and the neural network, the system comprising:
   a patch neural network configured to receive, for each of a plurality of patches generated by dividing the slide in a predetermined size, first image information to K-th image information corresponding to the patch through an input layer, and to output a patch-level diagnosis result indicating whether a disease exists in the patch; and a slide diagnosis engine configured to mark a patch determined as cancer as a result of patch-level diagnosis on each of the plurality of patches included in the slide, and outputting a slide-level diagnosis result indicating whether a disease exists in the slide on the basis of the marked result, wherein i-th image information, i being an arbitrary integer of $1<=i<=K$, is configured of at least one channel value corresponding to an i-th color model, and all of a first color model to a K-th color model are different color models.

7. A disease diagnosis method implemented in a system including a processor and a storage device storing a neural network, and using a slide of which biological tissue is disposed thereon and of which a biometric image is obtained therefrom, and the neural network, the method comprising the steps of:

generating, for each of a plurality of patches generated by dividing the slide in a predetermined size, first image information to K-th image information, wherein, K is an integer equal to or greater than 2, corresponding to the patch, wherein i-th image information, wherein i is an arbitrary integer of $1<=i<=K$, is configured of at least one channel value corresponding to an i-th color model, and all of a first color model to a K-th color model are different color models; and receiving, for each of the plurality of patches, the first image information to the K-th image information corresponding to the patch through an input layer, and outputting, by the system, a patch-level diagnosis result indicating whether a disease exists in the patch.

8. The method according to claim 7, wherein each of the first color model to the K-th color model is any one among a Red/Green/Blue (RGB) model, a Hue/Saturation/Blackness-Value (HSV) model, a Cyan-Magenta-Yellow-Black (CMYK) model, a Luma/Blue-Difference/Red-Difference (YCbCr) model, and a Gray model.

9. The method according to claim 7, further comprising the step of marking a patch determined as cancer as a result of patch-level diagnosis on each of the plurality of patches included in the slide, and outputting, by the system, a slide-level diagnosis result indicating whether a disease exists in the slide on the basis of the marked result.

10. The method according to claim 9, wherein the step of outputting a slide-level diagnosis result includes the steps of:

forming a plurality of clusters by clustering the patches determined as cancer in a predetermined manner;

receiving a plurality of cluster features as input values for each of the formed clusters, and outputting the slide-level diagnosis result of the slide including the clusters.

11. A disease diagnosis method implemented in a system including a processor and a storage device storing a neural network, and using a slide of which biological tissue is disposed thereon and of which a biometric image is obtained therefrom, and the neural network, the method comprising the steps of:

receiving, for each of a plurality of patches generated by dividing the slide in a predetermined size, first image information to K-th image information corresponding to the patch through an input layer, and outputting a patch-level diagnosis result indicating whether a disease exists in the patch; and marking a patch determined as cancer as a result of patch-level diagnosis on each of the plurality of patches included in the slide, and outputting, by the system, a slide-level diagnosis result indicating whether a disease exists in the slide on the basis of the marked result, wherein i-th image information, in which i is an arbitrary integer in the range of $1<=i<=K$, is configured of at least one channel value corresponding to an i-th color model, and all of a first color model to a K-th color model are different color models.

12. A non-transitory computer readable medium storing a computer program for performing the method according to claim 7.

13. A non-transitory computer readable medium storing a computer program for performing the method according to claim 11.

14. The method according to claim 11, wherein each of the first color model to the K-th color model is any one among a Red/Green/Blue (RGB) model, a Hue/Saturation/Blackness-Value (HSV) model, a Cyan-Magenta-Yellow-Black (CMYK) model, a Luma/Blue-Difference/Red-Difference (YCbCr) model, and a Gray model.

15. The method according to claim 11, wherein the step of outputting a slide-level diagnosis result includes the steps of:

forming a plurality of clusters by clustering the patches determined as cancer in a predetermined manner;

receiving a plurality of cluster features as input values for each of the formed clusters, and outputting the slide-level diagnosis result of the slide including the clusters.

* * * * *